United States Patent [19]

Markezich

[11] 4,329,287

[45] May 11, 1982

[54] HALO-(CARBONYLDIOXYARYL)ETHYLENES

[75] Inventor: Ronald L. Markezich, Williamsville, N.Y.

[73] Assignee: General Electric Company, Schenectady, N.Y.

[21] Appl. No.: 212,485

[22] Filed: Dec. 3, 1980

[51] Int. Cl.$^3$ ........................................... C07D 317/46
[52] U.S. Cl. .................................... 549/241; 568/726; 568/722; 549/240; 549/246
[58] Field of Search ..................................... 260/340.2

[56] References Cited

U.S. PATENT DOCUMENTS 4,097,538  6/1978  Factor et al. ...................... 568/726

Primary Examiner—Norma S. Milestone
Attorney, Agent, or Firm—Joseph T. Cohen; James C. Davis, Jr.

[57] ABSTRACT

Halo-(carbonyldioxyaryl)ethylenes are prepared by a catalytic process which comprises contacting a halo-bis(hydroxyaryl)ethylene, carbon monoxide, an oxidant, a base, and a Group VIIIB element selected from ruthenium, rhodium, palladium, osmium, iridium or platinum. The resulting halo-(carbonyldioxyaryl)-ethylenes are useful as flame retardents for thermoplastic polymeric materials.

3 Claims, No Drawings

HALO-(CARBONYLDIOXYARYL)ETHYLENES

BACKGROUND OF THE INVENTION

1. Field of the Invention

This invention relates to halo-(carbonyldioxyaryl)ethylenes which are prepared by contacting a halo-bis(hydroxyaryl)ethylene, carbon monoxide, an oxidant, a base and the Group VIIIB element selected from ruthenium, rhodium, palladium, osmium, iridium or platinum.

2. Description of the Prior Art

Halo-bis(hydroxydiaryl)ethylene compounds e.g., 1,1 dichloro-2,2-bis(4-hydroxyphenyl)ethylene, have been described in various patents and foreign publications including Factor et al., U.S. 4,097,538, issued June 27, 1978 and S. Porejko and Z. Wielgosz in the publication Polimery 13,55 (1968).

DESCRIPTION OF THE INVENTION

This invention embodies new halo-(carbonyldioxyaryl)-ethylenes which are prepared by contacting a halo-bis(hydroxyaryl)ethylene, carbon monoxide, an oxidant, a base, and the Group VIIIB element selected from ruthenium, rhodium, palladium, osmium, iridium or platinum.

The process of this invention involves the reaction of any halo-bis(hydroxyaryl)ethylene compound (hereinafter also referred to as "haloethylene") illustrated by the following general formula:

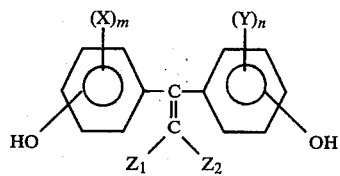

where X and Y are the same or different members selected from halogens or $C_{1-3}$ alkyls, (alkyl groups containing from 1 to 3 carbon atoms), m and n are whole numbers equal to from 1 to 3 inclusive, $Z_1$ is selected from hydrogen, chlorine, or bromine, $Z_2$ is selected from chlorine or bromine, and individually and independently the HO— groups are ortho, meta or para positioned relative to the

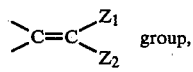

and each HO— group has at least a hydrogen—attached to each aryl ring—which is ortho positioned relative to each HO— group. Among the reactants within the scope of the above formula—mentioned for illustrative purposes—are those having the following formulas:

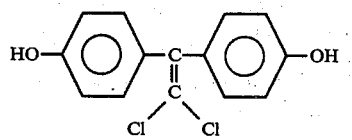

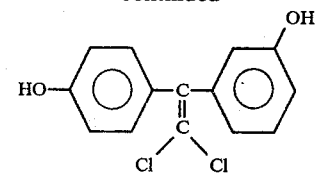

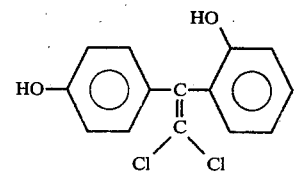

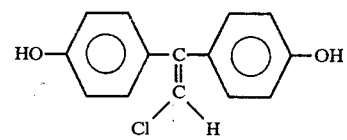

The new halo-(carbonyldioxyaryl)ethylenes are illustrated by the following general formulas:

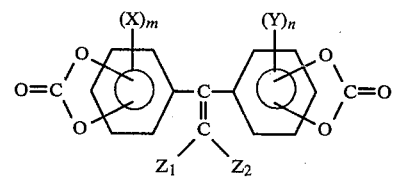

and

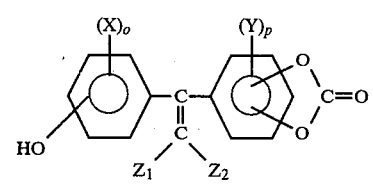

where X, Y, m, n, $Z_1$ and $Z_2$ are as defined in the general formula (1) above, o and p are whole numbers equal to 1 to 3 inclusive. Examples of subgeneric formulas coming within the scope of formulas (2) and (3) are

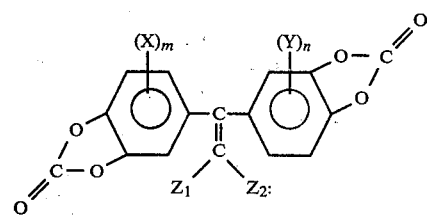

and

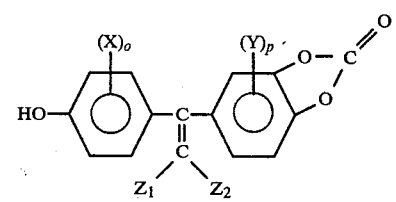

where X, Y, m, n, $Z_1$, $Z_2$, o, and p have the meaning above, and where the —OH group has at least a hydrogen attached to the aryl ring which is ortho-positioned relative to the —OH group. Among the specific reaction products within the scope of the above formula are those having the following formulas:

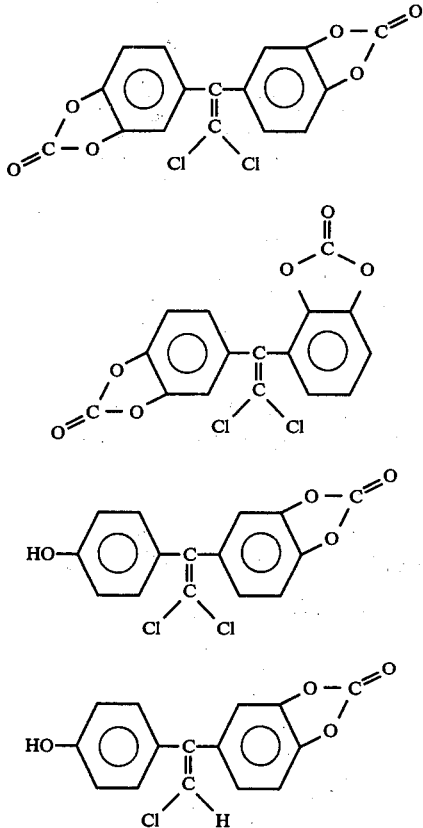

The Group VIIIB elements can be employed in any of their well known oxidation states as well as their zero value elemental, i.e. metallic form. Illustrative examples follow Ru, $RuCl_2$, $RuBr_2$, $Ru(CO)_2Cl_2$, etc., Pd, $PdCl_2$, $PdBr_2$, $PdI_2$, $(C_6H_5CN)_2PdCl_2$, etc. Rh, $Rh(CO)Cl_2$, $Rh(CO)Br_2$, etc., Os, $Os(CO)_3Cl_2$, $Os(CO)_3I_2$, etc., Ir, $IrCl_3$, $IrCl_3(CO)$, etc., Pt, $PtCl_2$, $PtBr_2$, $PtI_2$, $PtCl_2$—$(CNC_6H_5)_2$, etc. Further the Group VIIIB elements can be present in ionic, inorganic or organic compound or complex, etc. forms. Additional general information and specific examples are described in U.S. Pat. No. 4,201,721 whose descriptions are incorporated herein in their entirety by reference.

The process can be carried out in any basic reaction medium. Illustrative of bases that can be used are the following: elemental alkali or alkaline earth metals; basic quaternary ammonium, quaternary phosphonium or tertiary sulfonium compounds; alkali or alkaline earth metal hydroxides; salts of strong bases and weak acids; primary secondary or tertiary amines; etc. Specific examples of the aforementioned are sodium, potassium, magnesium metals, etc.; quaternary ammonium hydroxide, tetraethyl phosphonium hydroxide, etc.; sodium, potassium, lithium, and calcium hydroxide; quaternary phosphonium, tertiary sulfonium, sodium, lithium and barium carbonate; sodium acetate; sodium benzoate; sodium methylate; sodium thiosulfate; sodium sulfide; sodium tetrasulfide, sodium cyanide; sodium hydride; sodium borohydride; potassium fluoride; triethylamine; allyldiethylamine; benzyldimethylamine; dioctylbenzylamine; dimethylphenylamine, 1-dimethylamino-2-phenylpropane; N,N,N',N'-tetramethylenediamine; 2,2,6,6-tetramethylpyridine; N-methyl piperidine; 1,2,2,6,6-pentamethylpiperidine, etc.

The oxidant is oxygen which is preferably employed in the presence of a redox agent in order to enhance the reaction rate. The oxygen can be employed in any form e.g., air, gaseous oxygen, liquid oxygen, etc. Typical redox agents include compounds which catalyse the oxidation of the Group VIIIB elements from a lower oxidation state to a higher oxidation state, e.g. copper, iron, manganese, cobalt, mercury, lead, cerium, etc. Presently preferred redox agents are copper salts e.g., cupric chloride, cupric bromide, cupric sulfate, cupric acetate, etc.

The process can be carried out in the absence of any solvent, however, preferably is carried out in the presence of solvents of the general class: methylene chloride, ethylene dichloride, chloroform, carbon tetrachloride, tetrachloroethylene, nitromethane, hexane, 3-methylpentane, heptane, cyclohexane, methylcyclohexane, isooctane, p-cymene, cumene, decalin, toluene, benzene, diphenylether, dioxane, thiophene, dimethyl sulfide, ethyl acetate, tetrahydrofuran, chlorobenzene, anisol, bromobenzene, o-dichlorobenzene, methyl formate, isodobenzene, acetone, acetophenone, etc., including mixtures thereof.

Since water is a by-product of the reactions, enhanced reaction rates and/or conversions can be obtained by including in the process any means which removes water from the reaction environment. Accordingly, the use of azeotrope distillation techniques, drying agents, including Molecular Sieves is often beneficial.

Optionally the process can be carried out in the presence of an organic phase transfer agent. These phase transfer agents are well known and include illustratively "onium compounds" described by C. M. Starks in J.A.C.S. 93, 195 (1971), "crown ethers" described in Aldrichmmica ACTA 9, Issue #1 (1976) Crown Ether Chemistry-Principles and Applictions, G. W. Gokel and H. D. Durst, as well as C. J. Pederson in U.S. Pat. No. 3,622,577 and "chelated cationic salts" which include alkali or alkaline earth metal diamine halides. Specific illustrative examples are described in U.S. Pat. No. 4,201,721 whose descriptions are incorporated herein in their entity by reference.

Reaction temperatures of from 0° C. or less to 200° C. or more may be employed, however, from 0° C. to 50° C. is preferred.

Reaction time periods can vary widely, however, optimum yield and conversion related periods are 0.1 hour or less to 200 hours or more.

The process is carried out under positive carbon monoxide and oxygen pressure wherein the combination provides pressures within the range of from about 0.1 or less to 500 or more atmospheres.

Any amount of carbon monoxide, oxygen, redox agent, the Group VIIIB element, haloethylene, solvent, phase transfer agent, base, drying agent, etc. can be employed.

Generally effective amounts of the reactants are summarized hereinafter: redox agent to haloethylene—from about 0.0001:1 to 0.01:1.5; base to the Group VIIIB element—from 0.00001:1 to 0.5:1; the Group VIIIB element to haloethylene—from about 0.0001:1 to 0.01:1; solvent to haloethylene—from 0.5:99.5 to 99:5:0.5, phase transfer agent to the Group VIIIB element—from 0.00001:1 to 20:1. All of the above amounts are described on a mole ratio basis.

In order that those skilled in the art may better understand my invention, the following examples are given which are illustrative of the best mode of this invention, however, these examples are not intended to limit the invention in any manner whatsoever. In the examples, unless otherwise specified, all parts are by weight and the reaction products were verified by infrared spectrum, C-13 nuclear magnetic resonance and mass spectrometry.

EXAMPLE I

Into a 90-ml pressure vessel fitted with a magnetic stirrer was placed 1.475 g (5.3 mmole) of 1,1-dichloro-2,2-bis(4-hydroxyphenyl)ethylene, hereafter referred to as "dichloride" and described by formula 1 set out hereinafter

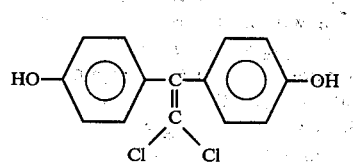

0.095 g (0.2 mmole) of bis(benzonitrile)palladium dibromide, 0.180 g (0.8 mmole) of cupric bromide, 0.220 g (1.71 mmole) of N,N-diisopropylethyl amine, 1.039 g of 4 A molecular sieves, and 20 ml of dichloromethane. The vessel was flushed with carbon monoxide and then charged with 31 psi of oxygen and 31 psi of carbon monoxide. After stirring at room temperature for 78 hours (more oxygen and carbon monoxide were added several times during the reaction), the solution was filtered, washed with dilute aqueous hydrochloric acid, water, and dried over anhydrous sodium sulfate. Concentration in vacuo afforded 1.73 g of a brown solid.

The HPLC showed the mixture to contain 67% of 1,1-dichloro-2,2-bis(3,4-catecholcarbonate)ethylene, hereafter of the formula set out hereinafter

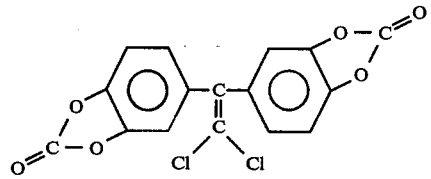

17% of 1,1-dichloro-2(4-hydroxyphenyl)-2(3,4-catechol carbonate)ethylene of the formula set out hereinafter

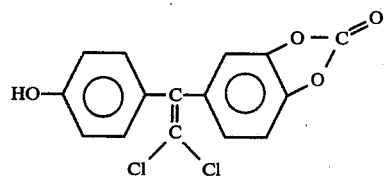

and 16% of dichloride oligomers. The $^{13}$nmr spectrum (CDCl$_3$) showed the material to contain 66% of the biscatechol carbonate of formula 2 and also smaller amounts of the monocatechol carbonate of formula 3.

The combined biscatechol carbonate, monocatechol carbonate, dichloride reaction product mixture was dissolved in dichloromethane and then added to hexane. The hexane solution was decanted from the precipitate and concentrated in vacuo to afford 0.718 g (37% yield) of the biscatechol carbonate of formula 2. Recrystallization of a sample from chloroform afforded off-white prisms, mp 138°–141°. IR(CHCl$_3$)—1849 and 1883 cm$^{-1}$. Mass Spectrum-m/e 368 (11%), 367 (12%), 366 (66%), 365 (18%), and 364 (100%). Calcd for C$_{16}$H$_6$O$_6$Cl$_2$; 363.9541. Found; 363.9524. $^{13}$C NMR (CDCl$_3$)—110.6, 126.4, 135.9, 111.6, 143.2, 143.4, 150.8, 137.6, and 121.1 ppm.

EXAMPLE II

Into a 265-ml pressure vessel fitted with a magnetic stirrer was placed 7.801 g (27.9 mmole) of the dichloride of formula 1 above, 0.476 g (1.0 mmole) of bis(benzonitrile)palladium dibromide, 0.894 g (4.0 mmole) of cupric bromide, 1.174 g (9.1 mmole) of N,N-diisopropylethylamine, 6.472 g of 4 A molecular sieves, and 100 ml of dichloromethane. The vessel was flushed with carbon monoxide and then charged with 30 psi of oxygen and 34 psi of carbon monoxide. After stirring at room temperture for 127 hours (more oxygen and carbon monoxide were added several times during the reaction), the solution was filtered, washed with dilute aqueous hydrochloric acid, water, and dried over anhydrous sodium sulfate. Concentration in vacuo afforded 9.4 g of a brown solid. The HPLC showed the mixture to contain 60% of the biscatechol carbonate of formula 2, 13% of the monocatechol carbonate of formula 3, 2% of the dichloride of formula 1, and 24% of dichloride oligomers. This material was dissolved in dichloromethane and then added to hexane. The solution was decanted from the precipitate and concentrated in vacuo to give 6.46 g (64% yield) of the biscatechol carbonate 2. The hexane/dichloromethane insoluble material was separated on a preparative HPLC column to give pure monocatechol carbonate 3. IR(CHCl$_3$)—1850 and 1838 cm$^{-1}$. Mass Spectrum- m/e 326 (17%), 325 (11%), 324 (61%), 323 (16%), and 322 (100%). Calcd for C$_{15}$H$_8$O$_4$Cl$_2$; 321.9800. Found; 321.9780. $^{13}$C NMR(CDCl$_3$)—110.2, 126.5, 137.1, 111.8, 142.6, 143.0, 138.4, 120.7, 131.0, 115.4, and 155.9 ppm.

The halo-(carbonyldixoyaryl)ethylenes can be used in their monomeric form as flame retardant additives or concentrates for normally flamable resinous materials. The carbonate portion associated with the aryl rings can be readily hydrolized to form polyhydroxy-substituted aryl-haloethylenes e.g., 1,1-dichloro-2,2-bis(3,4-dihydroxyphenyl)ethylene of the formula:

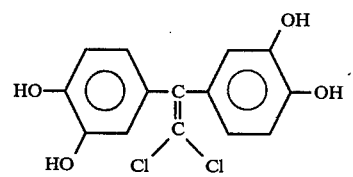

or 1,1-dichloro-2-(3,4-dihydroxyphenyl)-2-(4'-hydroxyphenyl)ethylene of the formula:

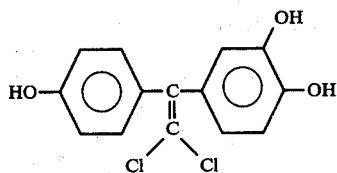

These polyhydroxy derivates can be converted readily to esters of monocarboxylic acids, can be reacted with ethylene oxide to form hydroxyethoxy derivatives e.g., 1,1-dichloro-2,2-bis(3,4-hydroxyethoxy)ethylene which in turn can be incorporated into either polyesters or polycarbonates, can be reacted with epichlorohydrin to form tetraglycidylether derivatives e.g., 1,1-dichloro-2,2-bis(3,4-hydroxyethoxy)ethylene tetraglycidylether, can be reacted with a mixture of acetic acid and acetic anhydride to prepare tetraacetate esters e.g., 1,1-dichloro-2,2-bis(3,4-diacetoxyphenyl)ethylene, can be reacted with allyl chloride to prepare 1,1-dichloro-2,2-bis(3,4-diallyloxyphenyl)ethylene, can be reacted with cyanogen bromide to replace the hydroxyl groups with —CN— groups in the preparation of 1,1-dichloro-2,2-bis(3,4-dicyanatophenyl)ethylene, etc. Further, the dihydroxy derivatives can be reacted with organo phosphites e.g. triethylphosphite, triphenylphosphite or phosphates e.g., triphenylphosphate to form halogenated phosphorous organic monomeric or polymeric materials.

The above mentioned monomeric halogenated derivative organic compounds can be employed as flame retardant additives, per se, for Engineering Thermoplastic Materials, e.g. NORYL ™ Resins, Lexan ™ Polycarbonate Resins, Valox ™ Polyester Resins, etc. or can be incorporated as flame retardant skeletal backbone segments—via the above mentioned reactive derivatives—within polyesters, polycarbonates, epoxy resins, polyethers, cyanurate polymers, halogenated phosphorous organic polymers, etc.

I claim:

1. A halo(carbonyldioxyaryl) ethylene compound selected from the class consisting of the general formulas:

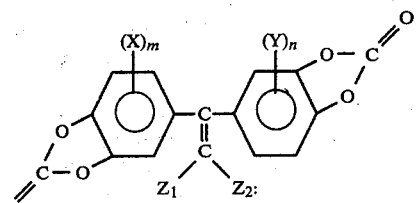

and

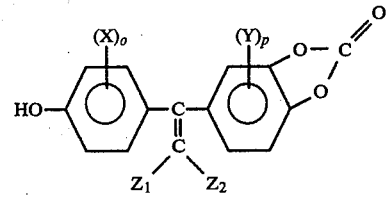

where X and Y are members independently selected from the class consisting of halogens or $C_{1-3}$ alkyls, m, n, o and p are a whole number equal to from 1 to 3, inclusive, $Z_1$ is hydrogen, chlorine or bromine and $Z_2$ is chlorine or bromine where the —OH group has at least a hydrogen attached to the aryl ring which is ortho positioned relative to the —OH group.

2. The compound of the formula:

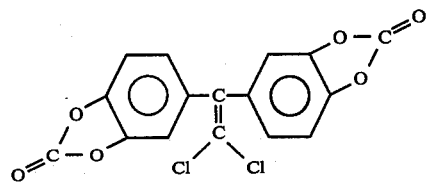

3. The compound of the formula:

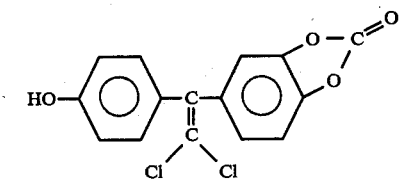

* * * * *